US00PP21395P2

(12) United States Plant Patent
Whetman

(10) Patent No.: US PP21,395 P2
(45) Date of Patent: Oct. 19, 2010

(54) *DIANTHUS* PLANT NAMED 'WP 05 PP 22'

(50) Latin Name: *Dianthus×hybrida*
Varietal Denomination: WP 05 PP 22

(76) Inventor: John Whetman, Deerpark Farm, Chudleigh, Newton Abbot (GB) TQ13 0NH ( * ) Notice: Subject to any disclaimer, the term of this patent is extended or adjusted under 35 U.S.C. 154(b) by 0 days.

(21) Appl. No.: 12/319,156

(22) Filed: Jan. 2, 2009

Related U.S. Application Data

(60) Provisional application No. 61/010,855, filed on Jan. 11, 2008.

(51) Int. Cl.
*A01H 5/00* (2006.01)

(52) U.S. Cl. ..... Plt./281

(58) Field of Classification Search ..... Plt./272, Plt./281
See application file for complete search history.

(56) References Cited

OTHER PUBLICATIONS

UPOV ROM, GTITM Plant Variety Database citation for 'WP05 PP22' PBR 20051756, filed Sep. 22, 2005, published Dec. 15, 2005.*

* cited by examiner

*Primary Examiner*—Annette H Para
*Assistant Examiner*—Louanne C Krawczewicz Myers

(57) ABSTRACT

A new cultivar of *Dianthus* plant named 'WP 05 PP 22' that is characterized by compact habit, grey-green foliage, and semi-double raspberry pink flowers. In combination these traits set 'WP 05 PP 22' apart from all other existing varieties of *Dianthus* known to the inventor.

2 Drawing Sheets

Genus: *Dianthus.*
Species: ×*hybrida.*
Denomination: 'WP 05 PP 22'.

BACKGROUND OF THE INVENTION

The present invention relates to a new and distinct cultivar of *Dianthus* that is grown for use as a flowering plant for pots and containers and as a hardy perennial for the garden border. The new cultivar is known botanically as *Dianthus×hybrida* and will be referred to hereinafter by the cultivar name 'WP 05 PP 22'.

'WP 05 PP 22' arose and was selected by the inventor in 2003 at the inventor's nursery in Houndspool, Dawlish, Devon, United Kingdom as a naturally occurring sport of *Dianthus* 'DEVON PP11' (U.S. Plant Pat. No. 14,919). 'WP 05 PP 22' exhibits upright compact habit, grey-green foliage, and an abundance of semi-double bright raspberry pink flowers.

The variety of *Dianthus* which is considered by the inventor to most closely resemble 'WP 05 PP 22' is the parent plant, *Dianthus* 'DEVON PP11'. Whereas 'DEVON PP11' produces semi-double bicolored (lavender and mid-pink) flowers, 'WP 05 PP 22' produces semi-double flowers which are uniformly colored bright raspberry pink.

Asexual reproduction of the new cultivar was first accomplished by the inventor in 2004 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP 05 PP 22'. These traits in combination distinguish this cultivar from all other commercial varieties known to the inventor. 'WP 05 PP 22' has not been tested under all possible conditions and phenotypic differences may be observed with variations in environmental, climatic and cultural conditions, however, without any variance in genotype.

1. *Dianthus* 'WP 05 PP 22' exhibits a compact habit.
2. *Dianthus* 'WP 05 PP 22' blooms profusely from May through October.
3. *Dianthus* 'WP 05 PP 22' exhibits semi-double flowers that are uniformly colored bright raspberry pink.
4. *Dianthus* 'WP 05 PP 22' exhibits grey-green foliage.
5. At maturity, the height of the foliage mound of *Dianthus* 'WP 05 PP 22' is 20 cm.
6. *Dianthus* 'WP 05 PP 22' is perennial and is hardy to −15° C.
7. *Dianthus* 'WP 05 PP 22' is suitable for use as a flowering plant in pots or border.

BRIEF DESCRIPTION OF THE DRAWINGS

The accompanying color drawings illustrate the overall appearance of the new *Dianthus* variety 'WP 05 PP 22' showing colors as true as it is reasonably possible to obtain in colored reproductions of this type. Colors in the drawings may differ from the color values cited in the detailed botanical description, which accurately describe the actual colors of the new variety 'WP 05 PP 22'.

The drawing labeled as FIG. 1 depicts an entire flowering plant.

Figure 1:
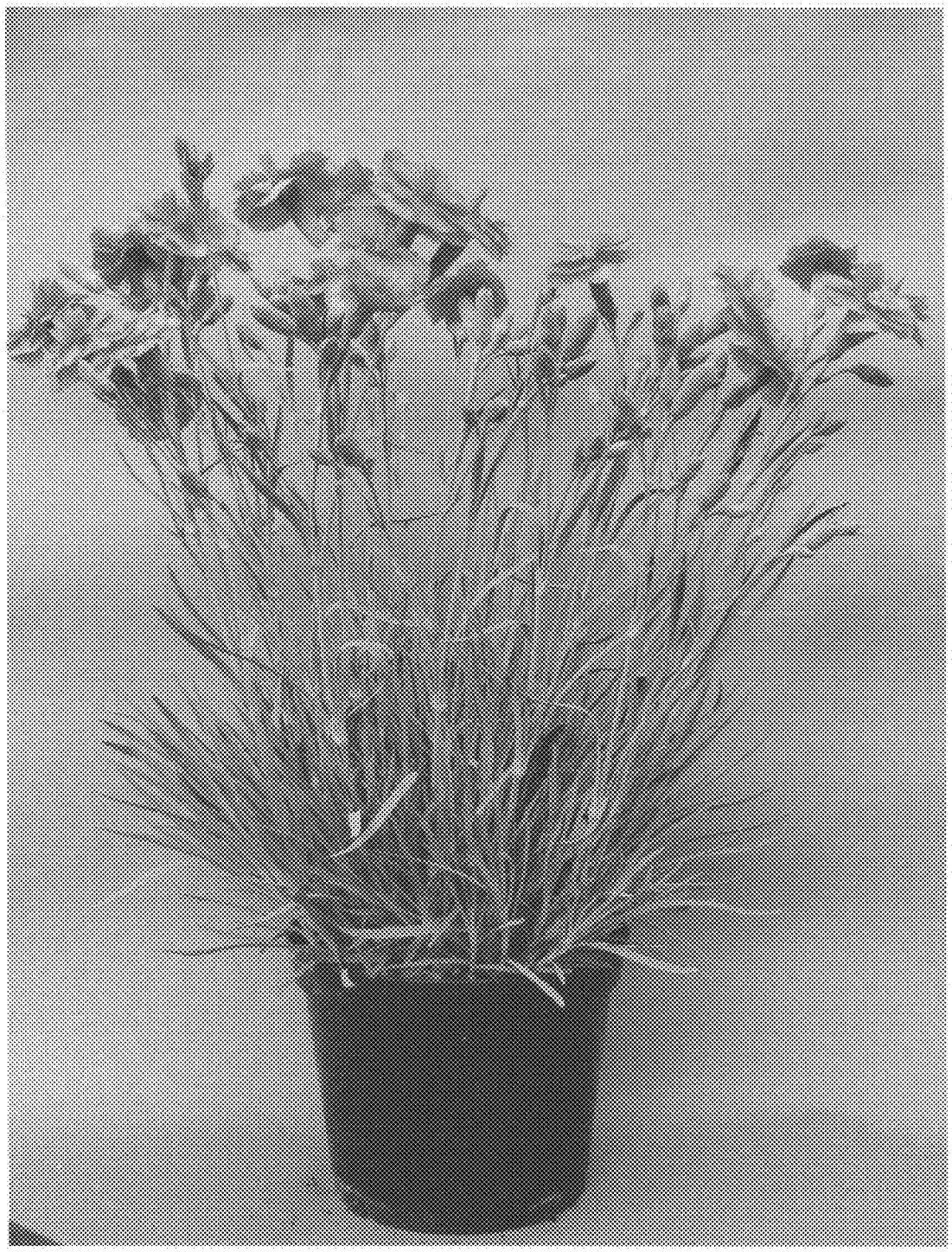
Figure 2:
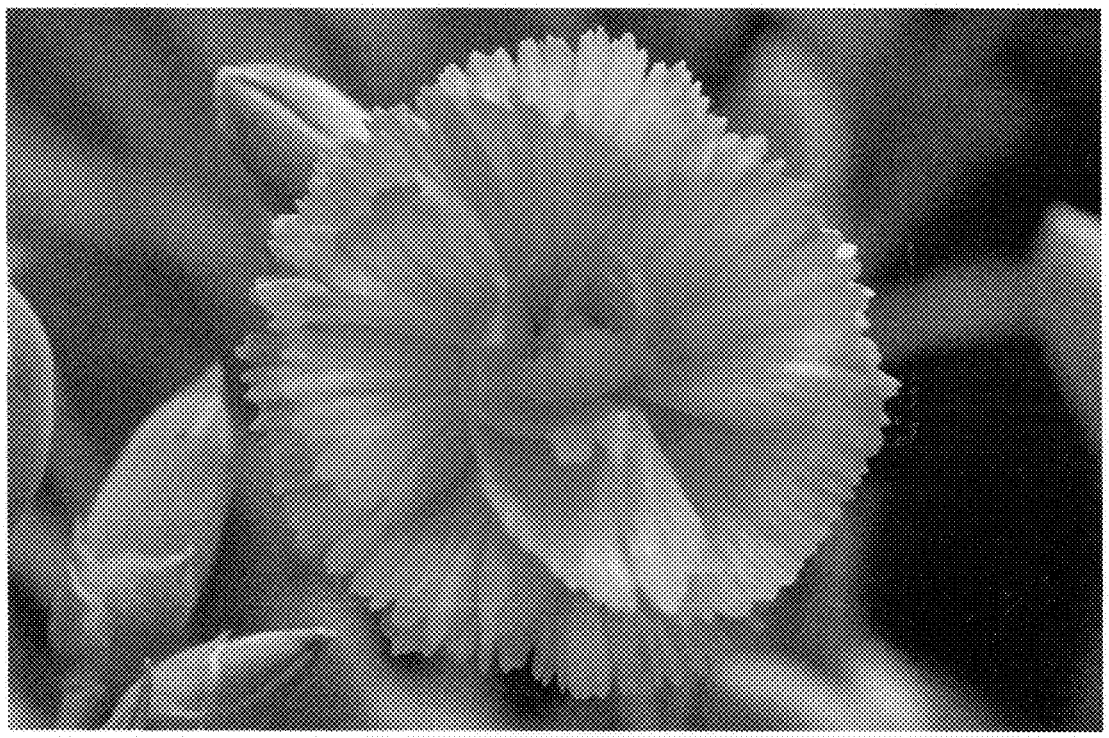

The drawing labeled as FIG. 2 depicts a close-up view of the flower.

All drawings were made of plants which were 9 months old and which had grown in 1.5-liter containers in an unheated glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP 05 PP 22'. Data was collected in spring and summer from plants which were 9 months old and which had been grown in 1.5-liter container plants in a frost-protected glasshouse in Devon, United Kingdom. The color determinations are in accordance with the 2007 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification: *Dianthus* 'WP 05 PP 22'.
Species: ×*hybrida*.
Common name: Garden pink.
Commercial classification: *Dianthus* hybrid.
Type: Perennial.
Use: Used as a flowering plant for pots and containers and for planting in the garden border.
Parentage: Naturally occurring sport of *Dianthus* 'DEVON PP11'.
Plant description:
- *Bloom period.*—May through October.
- *Plant habit.*—Compact mound with many branches and stems; upright growth.
- *Plant height.*—(*foliage mound*).—20 cm after 9 months.
- *Plant width.*—17 cm to 22 cm after 9 months.
- *Plant hardiness.*—Hardy to minus 15° Centigrade.
- *Root system.*—Fine fibrous roots.
- *Propagation.*—Propagation is accomplished using vegetative cuttings.
- *Cultural requirements.*—Grow in full sun, with moderate water, and well-drained moderately fertile soil. Remove dead flower heads to maintain flowering.
- *Diseases and pests.*—Susceptible to known *Dianthus* pests and disease but no other susceptibilities to pests or disease are known to the inventor.
- *Time and temperature needed to produce a rooted cutting.*—3 weeks are needed to produce roots on cuttings using a mist propagation unit with bottom heat of 21° Centigrade, and a minimum air temperature of 15° Centigrade.
- *Crop time.*—3 months starting in the early spring through summer and 6 months starting in the fall is needed to produce a finished container size plant from a well-rooted cutting.

Stem:
- *Shape.*—Cylindrical.
- *Stem dimensions.*—8 cm to 12 cm in height and 3 mm to 4 mm in diameter.
- *Stem surface.*—Glabrous and glaucous.
- *Stem color.*—145C.
- *Branching.*—Numerous shoots from the axils of the lower leaves.
- *Internode length.*—4 mm to 6 mm between nodes.
- *Node color.*—145C.
- *Node dimensions.*—4 mm in length and 3 mm to 4 mm in diameter.

Foliage:
- *Type.*—Evergreen.
- *Shape.*—Linear and straight.
- *Division.*—Simple.
- *Apex.*—Acute.
- *Base.*—Decurrent.
- *Venation.*—Not Prominent.
- *Margins.*—Entire.
- *Attachment.*—Sheathing.
- *Arrangement.*—Opposite or spiraling.
- *Surfaces* (*adaxial and abaxial*).—Glaucous.
- *Leaf dimensions.*—60 mm to 75 mm in length and 3 mm to 4 mm in width.
- *Leaf color* (*adaxial and abaxial surfaces*).—N189B.
- *Fragrance.*—Absent.

Buds (immediately prior to opening):
- *Shape.*—Conical.
- *Dimensions.*—15 mm-22 mm in length, 5 mm-8 mm in diameter.
- *Color.*—145B beneath bracteoles, 144B elsewhere except 144A at base.
- *Surface.*—Glabrous.

Flowers:
- *Inflorescence: Cymose.*
- *Number of flowers per stem.*—From 5 to 10.

Peduncles:
- *Dimensions.*—Length: 100 mm-150 mm (range for all flower stems). Diameter: 2 mm at base, 1.5 mm below terminal bud.
- *Strength.*—Stiff, wiry.
- *Angle*—Peduncles are erect and vertical.
- *Color.*—188A.
- *Pedicel dimensions.*—100 mm to 200 mm in length and 2 mm to 3 mm in width.
- *Pedicel strength.*—Erect.
- *Pedicel color.*—188A.
- *Flower development.*—In sequence from the uppermost bud.
- *Flower type.*—Salviform, semi-double and symmetrical.
- *Flower shape.*—Circular.
- *Flower profile.*—Reflexed.
- *Flower dimensions:* (*including calyx*).—35 mm in length and 40 mm in width.
- *Fragrance.*—Medium.
- *Petals.*—Number: 15-20 petals. Profile, upper part of corolla: Convex. Profile, lower part of corolla: Concave. Arrangement: Persistent, semi-double, apopetalous, overlapping. Margin: Serrate with indentations 0.5 mm to 2 mm deep. Apex: Rounded. Base: Attenuate. Texture: Soft. Shape: Obdeltoid. Surface: Glabrous. Dimensions: 35 mm to 40 mm in length and 15 mm to 20 mm in width. Color (adaxial surface): Ground color of blade: 67C. Band across blade: 61A Middle of strap: 145C. Base of strap: 145D. Color (abaxial surface): Ground color of blade: 64C. Band across blade: Absent. Middle of strap: 145C. Base of strap: 145D.
- *Calyx.*—Shape: Cylindrical. Longitudinal profile: Flat. Dimensions: 25 mm in length and 8 mm in diameter. Sepals: Fused. Number of sepals: 5. Sepal surface: Glaucous. Sepal apex: Acuminate. Sepal margin: Entire, smooth. Sepal color (both surfaces): 143A (apex) and 143C (blade). Anthocyanin: Absent. Splitting: Not observed.
- *Epicalyx.*—Bracts: 1 pair of 2. Shape of outer lobe: Acuminate. Dimensions: 10 mm in length and 8 mm in width. Color: 143A on the tip and 143C on the blade. Anthocyanin: Not present.
- *Bracteoles.*—Number: 2. Dimensions: 8 mm in length and 6 mm in width. Color: 143A on the tip and 143C on the blade. Anthocyanin: Not present. Lastingness of flower: Each individual flower lasts an average of 10 days at 20° C. on the plant.

Reproductive organs:

*Stamens.*—Number: 5-10. Filament color: N155D. Dimensions: 15 mm-20 mm in length and 0.5 mm in diameter.

*Anthers.*—Number: 5-10. Color: 84C. Dimensions: 3 mm-4 mm in length and 0.5 mm in diameter. Attachment: Basifixed.

*Pollen.*—Occasionally. Color: 11D.

*Pistil.*—Number: 2; length 30 mm-40 mm; color, white.

*Style.*—Number: 2. Shoulder: Absent. Color: NN155D. Dimensions: 25 mm to 30 mm in length and 1 mm in width.

*Stigma.*—Number: Single. Color: N66C. Dimensions: 5 mm to 8 mm above petals.

*Ovary.*—Position: Superior. Dimensions: 8 mm in length and 5 mm in diameter. Shape: Spindle. Color (adaxial): 145B. Color (abaxial): 145C.

*Seed.*—Number: 1-10. Dimensions: 3 mm in length and 2 mm in width. Color: 202A. Shape: Oval and flattened. Surface: Crinkled.

What is claimed is:

1. A new and distinct cultivar of *Dianthus* plant named 'WP 05 PP 22' as described and illustrated herein.

* * * * *